(12) United States Patent
O'Connor et al.

(10) Patent No.: US 7,645,275 B2
(45) Date of Patent: *Jan. 12, 2010

(54) VARIABLE STIFFNESS HEATING CATHETER

(75) Inventors: Michael J. O'Connor, Santa Clara, CA (US); David A. Ferrera, Manhattan Beach, CA (US); Matthew Connors, San Jose, CA (US)

(73) Assignee: Micrus Corporation, San Jose, CA (US)

( * ) Notice: Subject to any disclaimer, the term of this patent is extended or adjusted under 35 U.S.C. 154(b) by 304 days.

This patent is subject to a terminal disclaimer.

(21) Appl. No.: 11/433,242

(22) Filed: May 12, 2006

(65) Prior Publication Data

US 2006/0265036 A1 Nov. 23, 2006

Related U.S. Application Data (63) Continuation of application No. 10/930,588, filed on Aug. 31, 2004, now Pat. No. 7,066,931, which is a continuation of application No. 09/813,119, filed on Mar. 19, 2001, now Pat. No. 6,887,235, which is a continuation-in-part of application No. 09/275,485, filed on Mar. 24, 1999, now Pat. No. 6,352,531.

(51) Int. Cl.
  *A61B 18/04* (2006.01)
(52) U.S. Cl. ............... 606/27; 606/28; 606/32
(58) Field of Classification Search ............. 606/13–16, 606/27–49; 607/96–103; 604/915–921
  See application file for complete search history.

(56) References Cited

U.S. PATENT DOCUMENTS 679,671 A 7/1901 Hannigan

| | | | |
|---|---|---|---|
| 1,341,052 A | 5/1920 | Gale | |
| 1,621,159 A | 3/1927 | Evans | |
| 1,667,730 A | 5/1928 | Green | |

(Continued)

FOREIGN PATENT DOCUMENTS

CH 680 041 A5 6/1992

(Continued)

OTHER PUBLICATIONS

Christos A. Athanasoulis, M.D., The New England Journal of Medicine, May 15, 1980, "Therapeutic Applications of Angiography" pp. 1117-1125 (1 of 2).

(Continued)

*Primary Examiner*—Ahmed M Farah
(74) *Attorney, Agent, or Firm*—Fulwider Patton, LLP (57) ABSTRACT

The variable stiffness heating catheter includes a heating catheter shaft including at least one electrically conductive member, a reinforcing tube with apertures formed around the surface of the reinforcing tube, and at least one coaxial outer layer of a polymer, metal, or both for providing desired variations in stiffness along at least a portion of the length of the shaft. The apertures can be formed as axial or helical slits in the surface of the reinforcing tube, and the reinforcing tube can also be formed to be tapered at the point where the apertures are formed in the reinforcing tube to provide a heating catheter that is torqueable and pushable at the proximal end, yet soft and flexible at the distal end.

10 Claims, 6 Drawing Sheets

U.S. PATENT DOCUMENTS

| | | |
|---|---|---|
| 2,078,182 A | 4/1937 | MacFarland |
| 2,549,335 A | 4/1951 | Rahthus |
| 3,334,629 A | 8/1967 | Cohn |
| 3,417,746 A | 12/1968 | Moore et al. |
| 3,428,611 A | 2/1969 | Brotherton et al. |
| 3,572,891 A | 3/1971 | Longenecker |
| 3,649,224 A | 3/1972 | Anderson et al. |
| 3,670,721 A | 6/1972 | Fukami et al. |
| 3,788,304 A | 1/1974 | Takahashi |
| 3,868,956 A | 3/1975 | Alfidi et al. |
| 4,176,662 A | 12/1979 | Frazer |
| 4,241,979 A | 12/1980 | Gagen et al. |
| 4,248,910 A | 2/1981 | Pedain et al. |
| 4,327,734 A | 5/1982 | White, Jr. |
| 4,341,218 A | 7/1982 | Ü |
| 4,402,319 A | 9/1983 | Handa et al. |
| 4,441,495 A | 4/1984 | Hicswa |
| 4,450,246 A | 5/1984 | Jachimowicz |
| 4,473,665 A | 9/1984 | Martini-Vvedensky et al. |
| 4,494,531 A | 1/1985 | Gianturco |
| 4,503,569 A | 3/1985 | Dotter |
| 4,512,338 A | 4/1985 | Balko et al. |
| 4,522,195 A | 6/1985 | Schiff |
| 4,545,367 A | 10/1985 | Tucci |
| 4,585,000 A | 4/1986 | Hershenson |
| 4,638,803 A | 1/1987 | Rand |
| RE32,348 E | 2/1987 | Pevsner |
| 4,655,771 A | 4/1987 | Wallsten |
| 4,690,175 A | 9/1987 | Ouchi et al. |
| 4,692,139 A | 9/1987 | Stiles |
| 4,718,907 A | 1/1988 | Karwoski et al. |
| 4,748,986 A | 6/1988 | Morrison et al. |
| 4,753,222 A | 6/1988 | Morishita |
| 4,753,223 A | 6/1988 | Bremer |
| 4,768,507 A | 9/1988 | Fischell et al. |
| 4,791,913 A | 12/1988 | Maloney |
| 4,795,458 A | 1/1989 | Regan |
| 4,800,882 A | 1/1989 | Gianturco |
| 4,801,297 A * | 1/1989 | Mueller ...................... 604/523 |
| 4,808,164 A | 2/1989 | Hess |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,873,978 A | 10/1989 | Ginsburg |
| 4,884,579 A | 12/1989 | Engelson |
| 4,902,129 A | 2/1990 | Siegmund et al. |
| 4,904,048 A | 2/1990 | Sogawa et al. |
| 4,913,701 A | 4/1990 | Tower |
| 4,944,746 A | 7/1990 | Iwata et al. |
| 4,954,126 A | 9/1990 | Wallsten |
| 4,957,479 A | 9/1990 | Roemer |
| 4,957,501 A | 9/1990 | Lahille et al. |
| 4,969,709 A | 11/1990 | Sogawa et al. |
| 4,969,890 A | 11/1990 | Sugita et al. |
| 4,976,690 A | 12/1990 | Solar et al. |
| 4,984,581 A | 1/1991 | Stice |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,034,001 A | 7/1991 | Garrison et al. |
| 5,037,404 A | 8/1991 | Gold et al. |
| 5,037,427 A | 8/1991 | Harada et al. |
| 5,041,084 A | 8/1991 | DeVries et al. |
| 5,055,101 A | 10/1991 | McCoy |
| 5,064,435 A | 11/1991 | Porter |
| 5,071,407 A | 12/1991 | Termin et al. |
| 5,089,005 A | 2/1992 | Harada |
| 5,100,429 A | 3/1992 | Sinofsky et al. |
| 5,104,404 A | 4/1992 | Wolff |
| 5,108,407 A | 4/1992 | Geremia et al. |
| 5,122,136 A | 6/1992 | Guglielmi et al. |
| 5,133,364 A | 7/1992 | Palermo et al. |
| 5,133,731 A | 7/1992 | Butler et al. |
| 5,133,732 A | 7/1992 | Wiktor |
| 5,135,517 A | 8/1992 | McCoy |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,151,152 A | 9/1992 | Kaeufe et al. |
| 5,160,341 A | 11/1992 | Brenneman et al. |
| 5,160,674 A | 11/1992 | Colton et al. |
| 5,170,801 A | 12/1992 | Casper et al. |
| 5,171,233 A | 12/1992 | Amplatz et al. |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,184,627 A | 2/1993 | De Toledo |
| 5,186,992 A | 2/1993 | Kite, III |
| 5,192,290 A | 3/1993 | Hilal |
| 5,197,978 A | 3/1993 | Hess |
| 5,203,772 A | 4/1993 | Hammerslag et al. |
| 5,211,658 A | 5/1993 | Clouse |
| 5,217,440 A | 6/1993 | Frassica |
| 5,217,484 A | 6/1993 | Marks |
| 5,222,969 A | 6/1993 | Gillis |
| 5,222,970 A | 6/1993 | Reeves |
| 5,224,953 A | 7/1993 | Morgentaler |
| 5,226,911 A | 7/1993 | Chee et al. |
| 5,228,453 A | 7/1993 | Sepetka |
| 5,230,348 A | 7/1993 | Ishibe et al. |
| 5,234,456 A | 8/1993 | Silvestrini |
| 5,250,071 A | 10/1993 | Palermo |
| 5,258,042 A | 11/1993 | Mehta |
| 5,261,916 A | 11/1993 | Engelson |
| 5,266,608 A | 11/1993 | Katz et al. |
| 5,304,194 A | 4/1994 | Chee et al. |
| 5,308,342 A | 5/1994 | Sepetka et al. |
| 5,312,415 A | 5/1994 | Palermo |
| 5,334,193 A * | 8/1994 | Nardella ...................... 606/41 |
| 5,336,205 A | 8/1994 | Zenzen et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,356,388 A | 10/1994 | Sepetka et al. |
| 5,358,493 A | 10/1994 | Schweich, Jr. et al. |
| 5,360,835 A | 11/1994 | Sato et al. |
| 5,366,442 A | 11/1994 | Wang et al. |
| 5,372,587 A | 12/1994 | Hammerslag et al. |
| 5,378,236 A | 1/1995 | Seifert |
| 5,382,259 A | 1/1995 | Phelps et al. |
| 5,409,453 A | 4/1995 | Lundquist et al. |
| 5,411,475 A | 5/1995 | Atala et al. |
| 5,413,597 A | 5/1995 | Krajicek |
| 5,423,773 A | 6/1995 | Jimenez |
| 5,423,829 A | 6/1995 | Pham et al. |
| 5,425,723 A | 6/1995 | Wang |
| 5,425,806 A | 6/1995 | Doolan et al. |
| 5,437,632 A | 8/1995 | Engelson |
| 5,441,516 A | 8/1995 | Wang et al. |
| 5,443,478 A | 8/1995 | Purdy |
| 5,443,498 A | 8/1995 | Fontaine |
| 5,472,017 A | 12/1995 | Kovalcheck |
| 5,480,382 A | 1/1996 | Hammerslag et al. |
| 5,484,424 A | 1/1996 | Cottenceau et al. |
| 5,499,973 A | 3/1996 | Saab |
| 5,507,769 A | 4/1996 | Marin et al. |
| 5,507,995 A | 4/1996 | Schweich, Jr. et al. |
| 5,514,128 A | 5/1996 | Hillsman et al. |

| | | |
|---|---|---|
| 5,514,176 A | 5/1996 | Bosley, Jr. |
| 5,522,836 A | 6/1996 | Palermo |
| 5,525,334 A | 6/1996 | Ito et al. |
| 5,531,685 A | 7/1996 | Hemmer et al. |
| 5,531,716 A | 7/1996 | Luzio et al. |
| 5,533,985 A | 7/1996 | Wang |
| 5,536,235 A | 7/1996 | Yabe et al. |
| 5,540,680 A | 7/1996 | Guglielmi et al. |
| 5,540,712 A | 7/1996 | Kleshinski et al. |
| 5,540,713 A | 7/1996 | Schnepp-Pesch et al. |
| 5,545,210 A | 8/1996 | Hess et al. |
| 5,549,109 A | 8/1996 | Samson et al. |
| 5,549,624 A | 8/1996 | Mirigian et al. |
| 5,554,181 A | 9/1996 | Das |
| 5,562,641 A | 10/1996 | Flomenblit et al. |
| 5,562,698 A | 10/1996 | Parker |
| 5,569,245 A | 10/1996 | Guglielmi et al. |
| 5,571,848 A | 11/1996 | Mortensen et al. |
| 5,578,074 A | 11/1996 | Mirigian |
| 5,582,619 A | 12/1996 | Ken |
| 5,601,593 A | 2/1997 | Freitag |
| 5,603,991 A | 2/1997 | Kupiecki et al. |
| 5,605,162 A | 2/1997 | Mirzaee et al. |
| 5,607,445 A | 3/1997 | Summers |
| 5,614,204 A | 3/1997 | Cochrum |
| 5,622,665 A | 4/1997 | Wang |
| 5,624,461 A | 4/1997 | Mariant |
| 5,624,685 A | 4/1997 | Takahashi et al. |
| 5,636,642 A | 6/1997 | Palermo |
| 5,637,086 A | 6/1997 | Ferguson et al. |
| 5,637,113 A | 6/1997 | Tartaglia et al. |
| 5,638,827 A | 6/1997 | Palmer et al. |
| 5,639,277 A | 6/1997 | Mariant et al. |
| 5,643,251 A | 7/1997 | Hillsman et al. |
| 5,643,254 A | 7/1997 | Scheldrup et al. |
| 5,645,558 A | 7/1997 | Horton |
| 5,645,564 A | 7/1997 | Northrup et al. |
| 5,649,909 A | 7/1997 | Cornelius |
| 5,649,949 A | 7/1997 | Wallace et al. |
| 5,653,691 A | 8/1997 | Rupp et al. |
| 5,660,692 A | 8/1997 | Nesburn et al. |
| 5,662,621 A | 9/1997 | Lafontaine |
| 5,662,622 A | 9/1997 | Gore et al. |
| 5,662,712 A | 9/1997 | Pathak et al. |
| 5,666,968 A | 9/1997 | Imran et al. |
| 5,667,522 A | 9/1997 | Flomenblit et al. |
| 5,669,924 A | 9/1997 | Shaknovich |
| 5,670,161 A | 9/1997 | Healy et al. |
| 5,676,697 A | 10/1997 | McDonald |
| 5,690,643 A | 11/1997 | Wijay |
| 5,690,666 A | 11/1997 | Berenstein et al. |
| 5,690,671 A | 11/1997 | McGurk et al. |
| 5,693,086 A | 12/1997 | Goicoechea et al. |
| 5,695,111 A | 12/1997 | Nanis et al. |
| 5,695,480 A | 12/1997 | Evans et al. |
| 5,695,482 A | 12/1997 | Kaldany |
| 5,695,517 A | 12/1997 | Marin et al. |
| 5,695,518 A | 12/1997 | Laerum |
| 5,700,253 A | 12/1997 | Parker |
| 5,702,361 A | 12/1997 | Evans et al. |
| 5,702,414 A | 12/1997 | Richter et al. |
| 5,709,704 A | 1/1998 | Nott et al. |
| 5,711,909 A | 1/1998 | Gore et al. |
| 5,713,864 A | 2/1998 | Verkaart |
| 5,716,365 A | 2/1998 | Goicoechea et al. |
| 5,716,410 A | 2/1998 | Wang et al. |
| 5,718,711 A | 2/1998 | Berenstein et al. |
| 5,722,989 A | 3/1998 | Fitch et al. |
| 5,723,004 A | 3/1998 | Dereume et al. |
| 5,725,546 A | 3/1998 | Samson |
| 5,725,568 A | 3/1998 | Hastings |
| 5,733,294 A | 3/1998 | Forber et al. |
| 5,733,329 A | 3/1998 | Wallace et al. |
| 5,733,400 A | 3/1998 | Gore et al. |
| 5,735,816 A | 4/1998 | Lieber et al. |
| 5,738,666 A | 4/1998 | Watson et al. |
| 5,741,323 A | 4/1998 | Pathak et al. |
| 5,741,325 A | 4/1998 | Chaikof et al. |
| 5,743,905 A | 4/1998 | Eder et al. |
| 5,746,765 A | 5/1998 | Kleshinski et al. |
| 5,746,769 A | 5/1998 | Ton et al. |
| 5,749,837 A | 5/1998 | Palermo et al. |
| 5,749,849 A | 5/1998 | Engelson |
| 5,749,894 A | 5/1998 | Engelson |
| 5,749,921 A | 5/1998 | Lenker et al. |
| 5,755,773 A | 5/1998 | Evans et al. |
| 5,759,173 A | 6/1998 | Preissman et al. |
| 5,766,151 A | 6/1998 | Valley et al. |
| 5,766,167 A | 6/1998 | Eggers et al. |
| 5,769,796 A | 6/1998 | Palermo et al. |
| 5,769,828 A | 6/1998 | Jonkman |
| 5,782,809 A * | 7/1998 | Umeno et al. ............... 604/526 |
| 5,788,626 A | 8/1998 | Thompson |
| 5,788,653 A | 8/1998 | Lorenzo |
| 5,792,124 A | 8/1998 | Horrigan et al. |
| 5,797,842 A | 8/1998 | Pumares et al. |
| 5,797,920 A | 8/1998 | Kim |
| 5,797,957 A | 8/1998 | Palmer et al. |
| 5,800,455 A | 9/1998 | Palermo et al. |
| 5,800,508 A | 9/1998 | Goicoechea et al. |
| 5,807,354 A | 9/1998 | Kenda |
| 5,807,398 A | 9/1998 | Shaknovich |
| 5,814,016 A | 9/1998 | Valley et al. |
| 5,814,062 A | 9/1998 | Septka et al. |
| 5,817,126 A | 10/1998 | Imran |
| 5,817,152 A | 10/1998 | Birdsall et al. |
| 5,830,209 A | 11/1998 | Savage et al. |
| 5,938,623 A | 8/1999 | Quiachon et al. |
| 5,972,026 A | 10/1999 | Laufer et al. |
| 6,063,080 A * | 5/2000 | Nelson et al. ............... 606/41 |
| 6,074,374 A | 6/2000 | Fulton |
| 6,251,129 B1 | 6/2001 | Dobak, III et al. |
| 6,352,531 B1 * | 3/2002 | O'Connor et al. ............ 606/15 |
| 6,556,873 B1 | 4/2003 | Smits |
| 6,887,235 B2 * | 5/2005 | O'Connor et al. ............ 606/27 |
| 7,066,931 B2 * | 6/2006 | O'Connor et al. ............ 606/27 |

FOREIGN PATENT DOCUMENTS

| | | |
|---|---|---|
| DE | 4102550 A1 | 8/1991 |
| EP | 0 183 372 A1 | 6/1986 |
| EP | 0 382014 A1 | 8/1990 |
| EP | 608 853 A2 | 8/1994 |
| FR | 592.182 | 7/1925 |
| GB | 2 066 839 A | 7/1981 |
| WO | WO 87/02473 | 4/1987 |
| WO | WO 99-32918 | 7/1999 |

OTHER PUBLICATIONS

Christos A. Athanasoulis, M.D., The New England Journal of Medicine, May 22, 1980, "Therapeutic Applications of Angiography" pp. 1174-1179 (2 of 2).
Alex Berenstein, M.D. and Irvin I. Kricheff, M.D., "Catheter and Material Selection for Transarterial Embolization: Technical Considerations" Radiology, Sep. 1979; pp. 631-639.
O.A. Battista, et al. Journal of Applied Polymer Science 1967 "Colloidal Macromolecular Phenomena. Part II. Novel Microcrystals of Polymers" pp. 481-498.
Sadek K. Hilal, M.D. et al. Journal of Neurological Surgery "Therapeutic Percutaneous Embolization for Extra-Axial Vascular Lesions of the Head, Neck and Spine" Sep. 1975; pp. 275-287.
Stephen L. Kaufman, M.D. et al. Investigative Radiology, May-Jun. 1978, "Transcatheter Embolization With Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar Collagen", pp. 163-168.

Richard E. Latchaw, M.D. et al., Radiology (1979) "Polyvinyl Foam Embolization of Vascular and Neoplastic Lesions of the Head, Neck and Spine" pp. 669-679.

Stewart R. Reuter, M.D. et al. American Journal of Radiology, Sep. 1975, "Selective Arterial Embolization for Control of Massive Upper Gastrointestinal Bleeding" pp. 119-126.

Glenn H. Roberson, et al., American Journal of Radiology, Oct. 1979, "Therapeutic Embolization of Juvenile Angiofibroma" pp. 657-663.

Sidney Wallace, M.D. et al., Cancer, Oct. 1979, "Arterial Occlusion of Pelvic Bone Tumors"; pp. 322-325 & 661-663.

"Mechanical Devices for Arterial Occlusion" by C. Gianturco, M.D., et al., Jul. 1975, pp. 428-435.

"Therapeutic Vascular Occlusion Utilizing Steel Coil Technique: Clinical Applications" by Sidney Wallace, et al., Am J. Roentgenol (1976); pp. 381-387.

"Transcatheter Intravascular Coil Occlusion of Experimental Arteriovenous Fistulas", by James H. Anderson, et al., Am. J. Roentgenol, Nov. 1977, pp. 795-798.

"'Mini' Gianturco Stainless Steel Coils for Transcatheter Vascular Occlusion" by James H. Anderson, et al., From the Department of Diagnostic Radiology at the University of Texas System Cancer Center, Aug. 1978, pp. 301-303.

"A New Improved Coil for Tapered-Tip Catheter for Arterial Occlusion" by Vincent P. Chuang, M.D., et al., May 1980, pp. 507-509.

International Search Report Dated Jun. 10, 1999.

"Retrievable Gianturco-Coil Introducer" by Jeffrey Hawkins, et al., Radiology, Jan. 1986; vol. 158:262-264.

* cited by examiner

VARIABLE STIFFNESS HEATING CATHETER

RELATED APPLICATIONS

This is a continuation of application Ser. No. 10/930,588, filed Aug. 31, 2004, now Pat. No. 7,066,931, which is a continuation of application Ser. No. 09/813,119, filed Mar. 19, 2001, now U.S. Pat. No. 6,887,235, which is a continuation-in-part of application Ser. No. 09/275,485 filed, Mar. 24, 1999, now U.S. Pat. No. 6,352,531.

BACKGROUND OF THE INVENTION

1. Field of the Invention

This invention relates generally to interventional medical devices, and more particularly concerns a heating catheter having variable stiffness for enhanced performance of the catheter shaft when used with or without a guide catheter, as a part of a therapeutic system or for delivery of medical devices.

2. Description of Related Art

Conventional minimally invasive catheter based therapies typically require guide wires that are one to two meters long extending through a longitudinal lumen in the catheter, and that are torqueable and pushable at the proximal end, yet soft and flexible at the distal end. Many such guidewires are made of stainless steel or the like, and are ground to tapers which provide the desired bending properties along the guidewire. Recently, numerous minimally invasive sensing and actuation procedures have been developed which benefit from the qualities of fiber optics to deliver optical light or power to the distal tip of the fiber optic. However, conventional fiber optic technology has not been easily adaptable to such applications, particularly when the fiber optic must also act as a guidewire, either within a catheter or as a stand-alone device, since fiber optics, when used alone, are not very torqueable, pushable or resilient when compared to guide wires made from a variety of other, more rigid, materials. Also, small diameter fiber optics are quite "floppy", while larger diameter fibers can be too stiff to maneuver through sharp bends, and the use of fiber optics as guidewires or pushers within catheters can thus be difficult and quite technique sensitive.

An abdominoscope is known that includes a tubular sheath having a series of strips separated by longitudinal slots, and an elongate, steerable, flexible medical implement is also known that has a tubular body with a controllable steering region formed from flexible steering ribbons made of flexible materials, such as Nitinol, spring steel, nylon, or other plastic material. In addition, a steerable medical probe is also known that has a torque tube with spaced apart slots to impart additional flexibility to the torque tube, with a thin-walled connecting portion serving as a rib or backbone. However, there remains a need for a way of creating variable stiffness along a heating catheter, other than a fiber optic for example, without a decrease in the torquability and pushability of the heating catheter shaft.

It would also be desirable to provide a heating catheter shaft with variable stiffness to allow such heating catheters to be more pushable at the proximal end and more trackable at the distal end, and to make the use of heating catheters in catheter-based therapies more straightforward and less technique sensitive. The present invention addresses these and numerous other needs.

SUMMARY OF THE INVENTION

Briefly, and in general terms, the present invention provides for a variable stiffness heating catheter shaft formed from a heating catheter and a reinforcing tube over at least a portion of the heating catheter, with apertures being formed around the surface of the reinforcing tube and extending in a direction between the proximal and distal ends of the heating catheter, to provide variable stiffness to the heating catheter shaft. Typically, such a heating catheter shaft can be formed from one or more electrically conductive members or the like which alone have physical characteristics that are undesirable for guidewires or pusher devices. By use of the invention, a variable stiffness heating catheter shaft can be made which is more pushable at the proximal end and more trackable at the distal end, with the capability to provide a wide range of predictable variations in stiffness and other structural parameters over the length of the shaft. A variable stiffness heating catheter constructed according to the invention can be used in conjunction with a guide catheter or as a flow directed, stand alone catheter.

By using the construction according to the invention, coating or heat shrinking a heat shrinkable material on the outside diameter of the heating catheter shaft will improve tracking of the device, and a taper can also be ground onto the heating catheter shaft to yield a shaft with a stiffer, more manageable, proximal end and a softer, more maneuverable, distal tip. The variable stiffness heating catheter advantageously can also thus be constructed from a minimum number of components, with the apertures in the reinforcing tube eliminating the need for a braid or transitional sections from the stiffer proximal zone to the softer distal zone.

The invention accordingly provides in a presently preferred embodiment for a variable stiffness heating catheter for use in vascular interventional therapy, such as for use within a tortuous, small diameter vessel such as those found in the vasculature of the brain. The variable stiffness heating catheter comprises at least one electrically conductive member having a proximal end and a distal end, a reinforcing tube attached to the at least one electrically conductive member, with the at least one electrically conductive member extending through the reinforcing tube, and the reinforcing tube having a surface defining a plurality of apertures extending in a direction between said proximal and distal ends of said heating catheter, and at least one coaxial outer layer of a polymer, metal, or both provided over at least a portion of the reinforcing tube and the at least one electrically conductive member, for providing desired variations in stiffness along at least a portion of the length of the shaft. In a presently preferred embodiment, the one or more electrically conductive members can be a pair of such electrically conductive wires. The reinforcing tube is preferably a metal tube, such as a hypo tube, and can be formed of stainless steel or an alloy of nickel and titanium, for example.

In one presently preferred embodiment, the apertures can be formed as longitudinal, axial slits, slots, channels, or grooves in the surface of the reinforcing tube, and in an alternate preferred embodiment, the apertures can be formed as helical or radial slits, slots, channels, or grooves in the surface of the reinforcing tube, providing variable stiffness to the heating catheter. The outer surface of the reinforcing tube can also be formed to be tapered at the point where the apertures are formed in the reinforcing tube, particularly at a distal portion of the heating catheter, to provide a heating catheter that is torqueable and pushable at the proximal end, yet soft and flexible at the distal end. Alternatively, the apertures can be formed transversely in the surface of the reinforcing tube in an area where such a configuration will produce desired results.

The one or more coaxial layers can be formed of heat shrink polymeric material, such as polyethylene, polytetrafluoroethylene (PTFE) polyethylene terephthalate (PET), polyetherethylketone (PEEK), polyphenylenesulfide (PPS) or any of a variety of other polymers which can be fabricated into a structure and necked or shrunk over a shaft, or can be formed of metal. While the invention can effectively use tubes which are placed over the exterior of the heating catheter shaft and then heat shrunk or bonded by adhesive to the heating catheter shaft, it is also contemplated that the heating catheter shaft can be reinforced by other longitudinally extending additional structures with varying cross sections for certain specific applications.

The heat shrink tubing is placed on the heating catheter shaft, and then heat can be applied to the heat shrink tubing, resulting in shrinkage of the heat shrink tubing to encapsulate the heating catheter shaft. The structure formed by the apertures in the surface of the reinforcing tube, in combination with the distal taper of the reinforcing tube and outer coaxial sheath, allows the proximal part of the composite shaft to be relatively stiff, and the distal tip to be flexible and soft. A variety of other techniques can be used within the scope of the invention to accomplish the variable stiffness of the heating catheter.

These and other aspects and advantages of the invention will become apparent from the following detailed description and the accompanying drawings, which illustrate by way of example the features of the invention.

DETAILED DESCRIPTION OF THE PREFERRED EMBODIMENTS

Modern interventional medical procedures have relied on ever smaller and more flexible devices to reach areas requiring treatment which were previously inaccessible to conventional devices, such as by the placement of vasoocclusive devices in tiny areas of damaged vasculature such as aneurysms or ruptures in arteries in the brain. Some devices to treat such areas use optical fibers to carry light energy to remote locations at the distal end of the heating catheter, but certain limitations have been found in currently available optical fibers for those purposes.

For example, conventional heating catheter technology has not been easily adaptable to catheter based imaging, treatments such as "thrombolyzing" blood or cutting tissue, or to the delivery of therapeutic agents, such as timed release agents, or embolics, since optical fibers, when used as a stand alone structural device, are not very torqueable, pushable or resilient. Small diameter optical fibers of the type most useful for such therapies frequently can become too floppy, while larger diameter fibers can be too stiff to maneuver through sharp bends, and for these reasons, the use of optical fibers as stand alone guidewires or catheters can be difficult and technique sensitive. Also, since there are practical limits to the diameter of the fiber for specific applications, the use of reinforced guide catheters with longitudinal lumens through which the heating catheter passes can place important restrictions on how small such an assembly can be. Further, if the heating catheter is to be used with both a guidewire and a guiding catheter, there are limits imposed on the techniques that can be employed because of the necessarily larger diameter of such an assembly to accommodate the requirements of the two different shafts within the catheter.

Figure 1A:
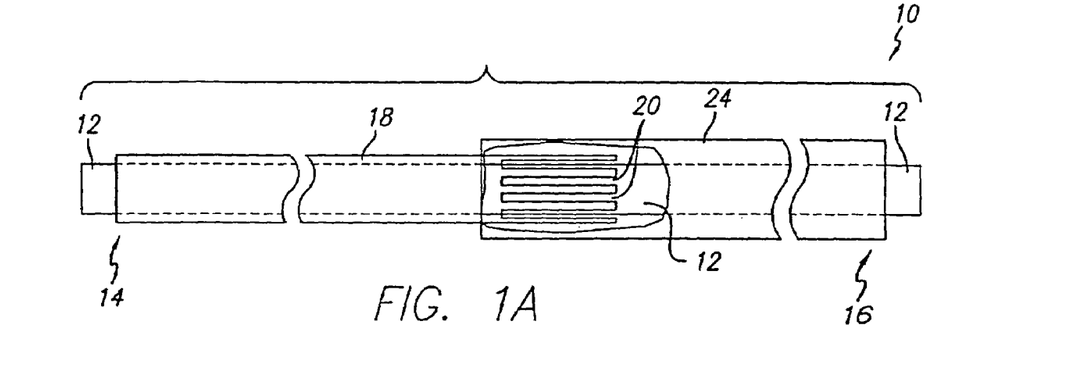
FIG. 1A is a schematic view of a first preferred embodiment of a variable stiffness heating catheter according to the invention.

As is illustrated in the drawings, which are provided for the purposes of illustration and not by way of limitation, one preferred embodiment of the invention illustrated in FIGS. 1A to 2D provides for a variable stiffness heating catheter 10 that comprises at least one electrically conductive member 12 having a proximal end 14 and a resistive heating element (not shown) connected to the one or more electrically conductive members at a distal end 16. The at least one electrically conductive member 12 is surrounded by a reinforcing tube 18, such as a metal tube, which can for example be a stainless steel hypo tube, although the reinforcing tube may also be formed of a nickel titanium alloy, such as NITINOL. The reinforcing tube can be cylindrical as shown in FIG. 1, or may be tapered along its length, either in steps or continuously in order to provide a desired stiffness and pushability. In one presently preferred embodiment, the reinforcing tube is advantageously provided with a plurality of longitudinal, axially oriented apertures, such as slits, slots, channels, or grooves 20 formed around the surface of a portion of the reinforcing tube to provide a heating catheter that is torqueable and pushable at the proximal end, yet soft and flexible at the distal end. As is illustrated in FIG. 1A, the apertures can be formed in the surface of the reinforcing tube, such as by laser cutting, for example, and allow the reinforcing tube to have the same diameter, or a tapering diameter, with variable stiffness. In a presently preferred alternate embodiment illustrated in FIG. 1B, in which like elements are designated with like reference numerals, the apertures can be formed as groups 20' of round holes 21, arranged so as to be longitudinal, and axially oriented around the surface of a portion of the reinforcing tube, so as to provide a heating catheter that is torqueable and pushable at the proximal end, yet soft and flexible at the distal end. As is illustrated in FIGS. 1C and 1D, the one or more electrically conductive members can be a pair of such electrically conductive wires 12', for example.

Figure 2A:
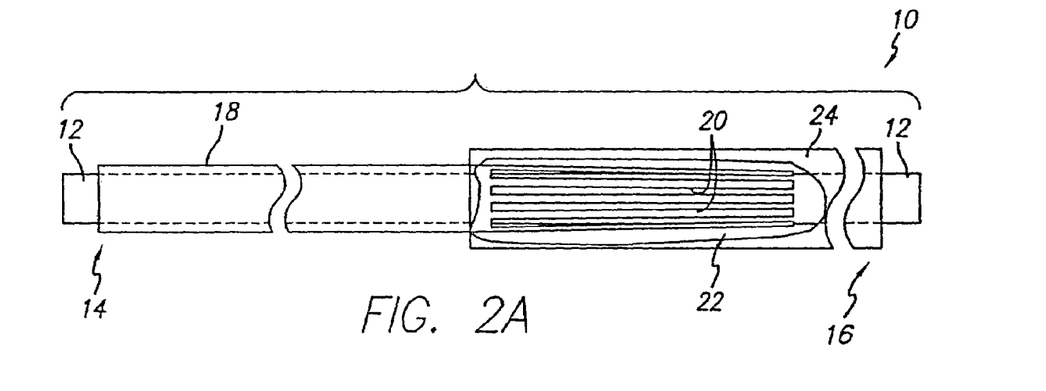
FIG. 2A is a schematic view of a third preferred embodiment of a variable stiffness heating catheter according to the invention.
Figure 2B:
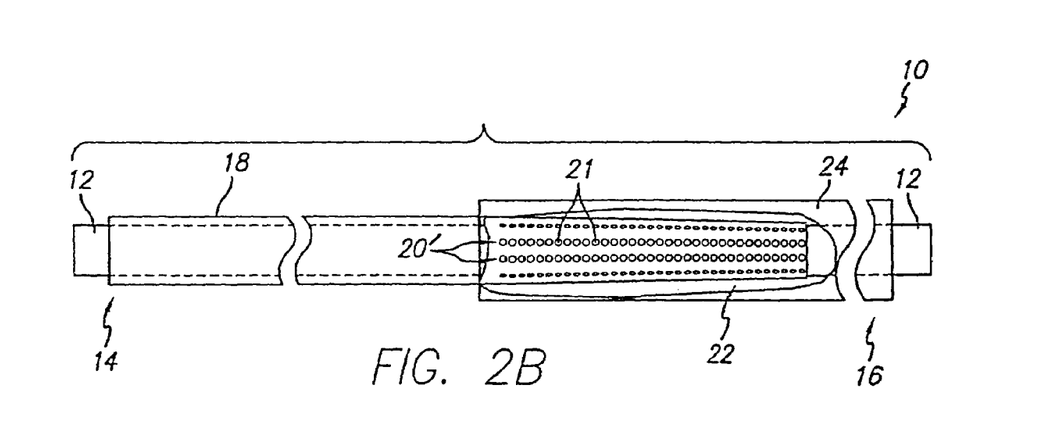
FIG. 2B is a schematic view of fourth preferred embodiment of a variable stiffness heating catheter according to the invention.
Figure 2C:
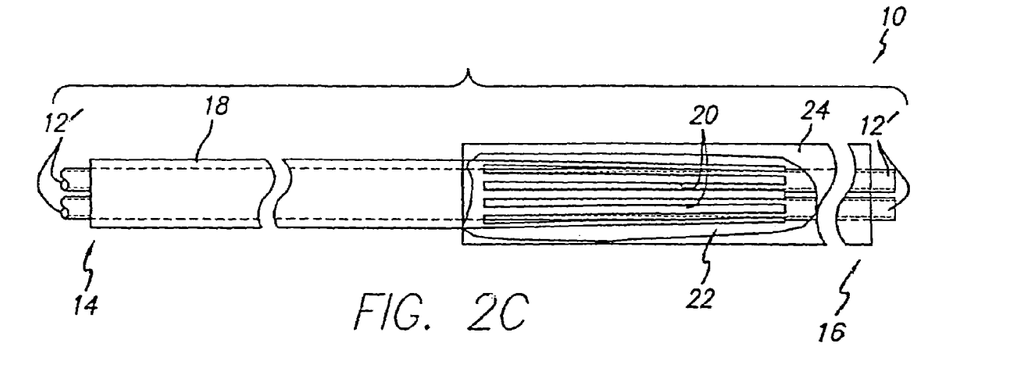
FIG. 2C is a sectional view of a variant of the third preferred embodiment of the catheter shaft of FIG. 2A illustrating a pair of electrically conductive members.
Figure 2D:
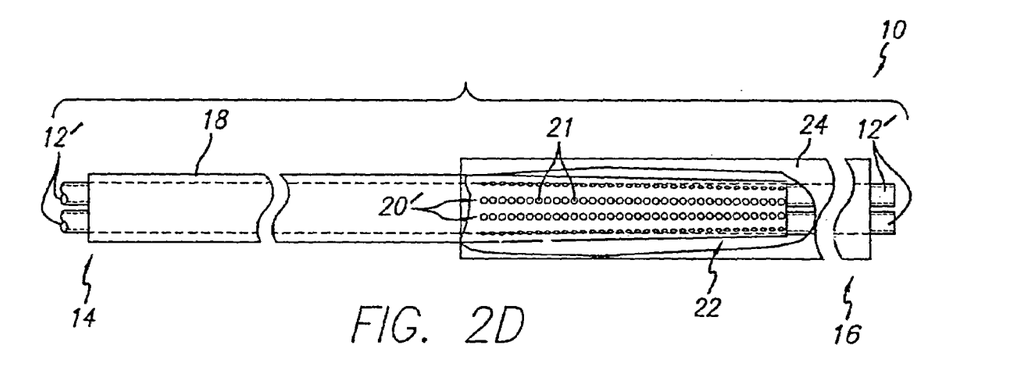
FIG. 2D is a sectional view of a variant of the fourth preferred embodiment of catheter shaft of FIG. 2B illustrating a pair of electrically conductive members.

Alternatively, as is illustrated in FIG. 2A, in which like elements are designated with like reference numerals, the apertures can be formed in the surface of the reinforcing tube by grinding. In another presently preferred aspect illustrated in FIG. 2A, the outer surface of the reinforcing tube can also be formed to have a taper 22 at the point where the apertures are formed in the reinforcing tube, such as by grinding or laser cutting, particularly at a distal portion of the heating catheter, to provide a heating catheter that is torqueable and pushable at the proximal end, yet soft and flexible at the distal end. In a presently preferred alternate embodiment illustrated in FIG. 2B, in which like elements are designated with like reference numerals, the apertures can be formed as groups 20' of round holes 21, such as by laser cutting, at a distal portion of the heating catheter, to provide a heating catheter that is torqueable and pushable at the proximal end, yet soft and flexible at the distal end. As is illustrated in FIGS. 2C and 2D, the one or more electrically conductive members can be a pair of such electrically conductive wires 12', for example.

Referring to FIGS. 1A, 1B, 1C, 1D, 2A, 2B, 2C and 2D, in a currently preferred embodiment, at least one coaxial outer covering or sheath 24 is also provided over at least a portion of the heating catheter and reinforcing tube, for providing desired variations in stiffness along at least a portion of the length of the shaft. Such an outer sheath is currently preferably a heat shrink polymer, such as polyethylene, PTFE, PEEK, PET or PPS, for example, although other similar heat shrink polymers may also be suitable. Alternatively, the outer sheath can be a metal tube, such as a metal tube formed from a nickel titanium alloy, for example, that can be bonded adhesively over the outer surface of the heating catheter, such as by cyanoacrylate adhesive. Alternatively, where the reinforcing tube is sufficient to provide the desired variable stiffness characteristics to the heating catheter, the outer sheath may be omitted.

Figure 1B:
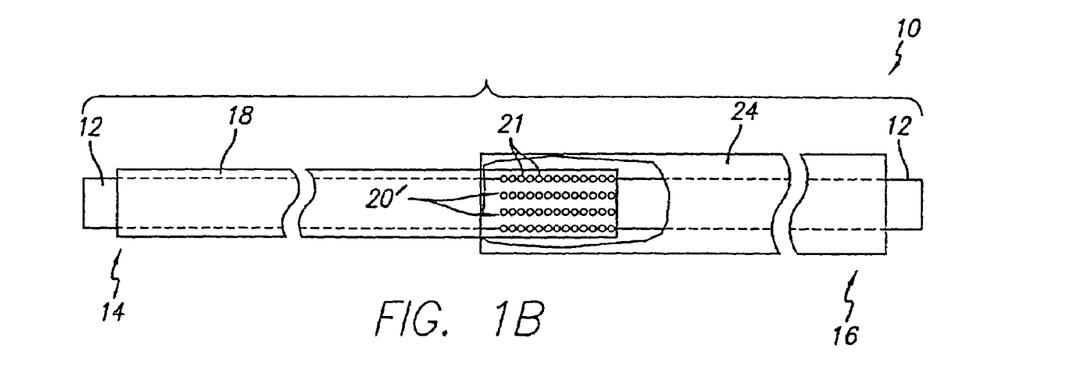
FIG. 1B is a schematic view of a second preferred embodiment of a variable stiffness heating catheter according to the invention.
Figure 1C:
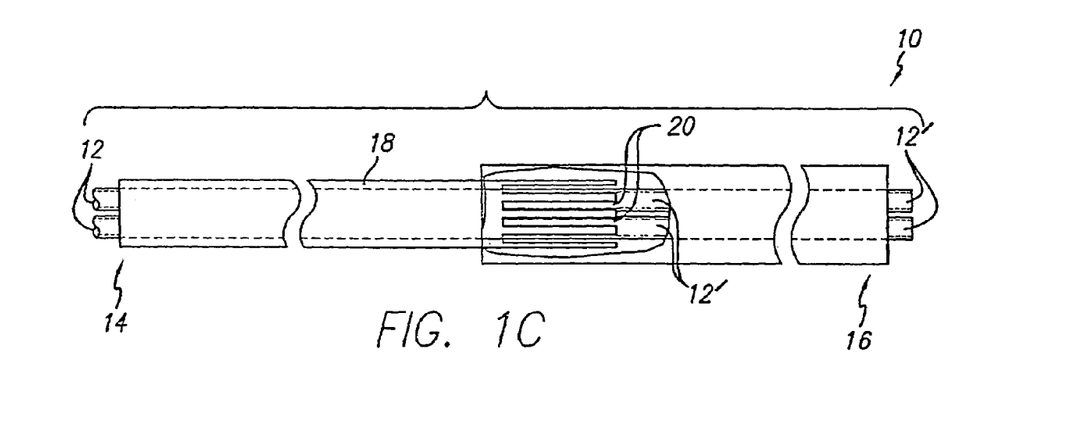
FIG. 1C is a sectional view of a variant of the first preferred embodiment of the catheter shaft of FIG. 1A illustrating a pair of electrically conductive members.
Figure 1D:
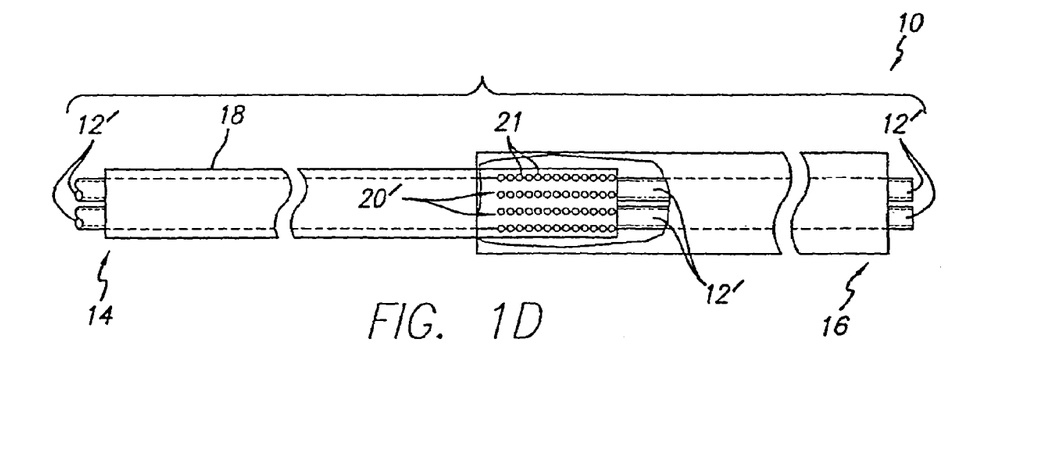
FIG. 1D is a sectional view of a variant of the second preferred embodiment of catheter shaft of FIG. 1B illustrating a pair of electrically conductive members.
Figure 3A:
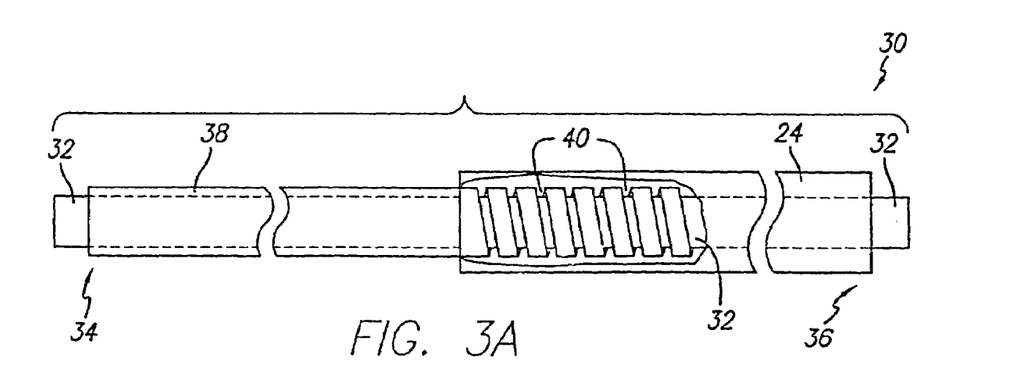
FIG. 3A is a schematic view of a fifth preferred embodiment of a variable stiffness heating catheter according to the invention.

In another presently preferred embodiment, illustrated in FIG. 3A, a variable stiffness heating catheter 30 is provided that comprises at least one electrically conductive member 32 having a proximal end 34 and a resistive heating element (not shown) connected to the one or more electrically conductive members at a distal end 36. The at least one electrically conductive member 32 is surrounded by a reinforcing tube 38, such as a metal tube, which can for example be a stainless steel hypo tube, although the reinforcing tube may also be formed of a nickel titanium alloy, such as NITINOL. The reinforcing tube can be cylindrical as shown in FIGS. 1A and 1B, or may be tapered along its length, either in steps or continuously in order to provide a desired stiffness and pushability. At least one coaxial outer covering of sheath 24 is also provided over at least a portion of the at least one electrically conductive member and reinforcing tube, as discussed above. In one presently preferred embodiment, the reinforcing tube is advantageously provided with a plurality of helically arranged apertures 40 formed as slits, channels or grooves around the surface of a portion of the reinforcing tube to provide a heating catheter that is torqueable and pushable at the proximal end, yet soft and flexible at the distal end. Alternatively, the apertures may be radially arranged apertures formed as slits, channels or grooves.

Figure 3B:
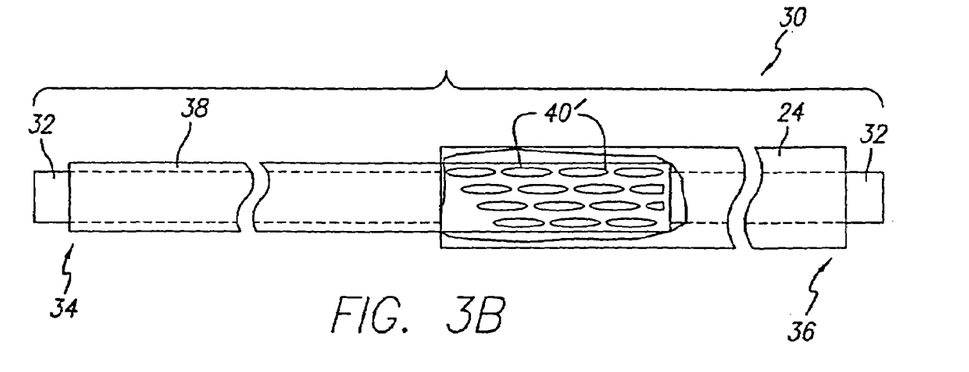
FIG. 3B is a schematic view of a sixth preferred embodiment of a variable stiffness heating catheter according to the invention.
Figure 3C:
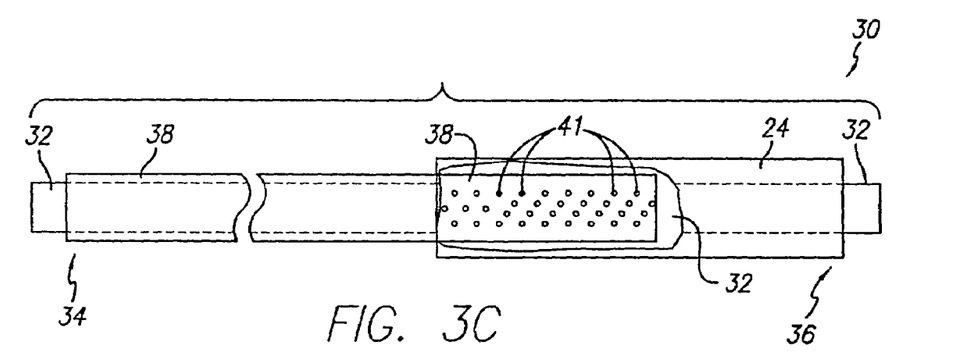
FIG. 3C is a schematic view of a seventh preferred embodiment of a variable stiffness heating catheter according to the invention.
Figure 3D:
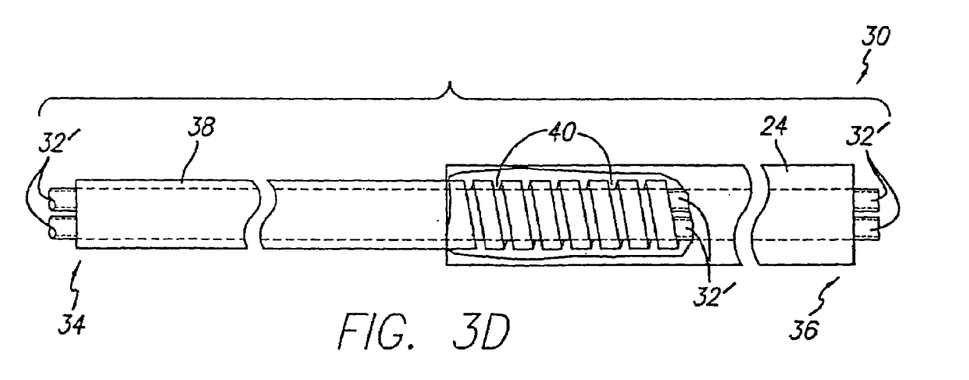
FIG. 3D is a sectional view of a variant of the fifth preferred embodiment of the catheter shaft of FIG. 3A illustrating a pair of electrically conductive members.
Figure 3E:
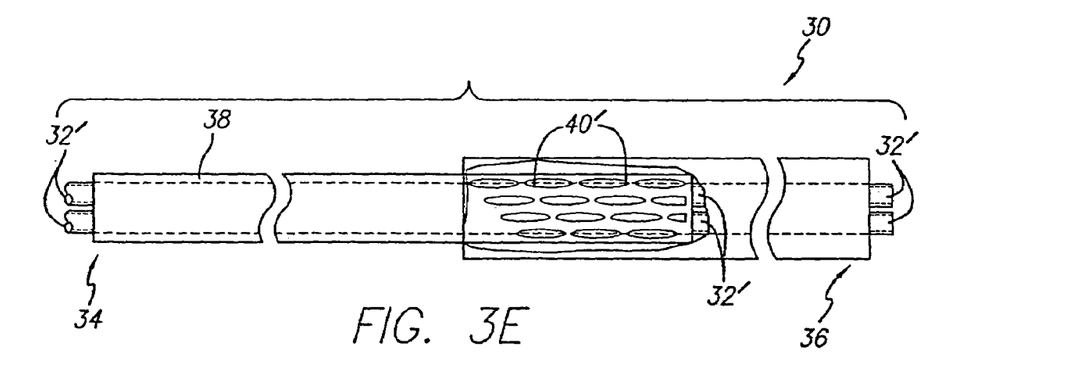
FIG. 3E is a sectional view of a variant of the sixth preferred embodiment of catheter shaft of FIG. 3B illustrating a pair of electrically conductive members.
Figure 3F:
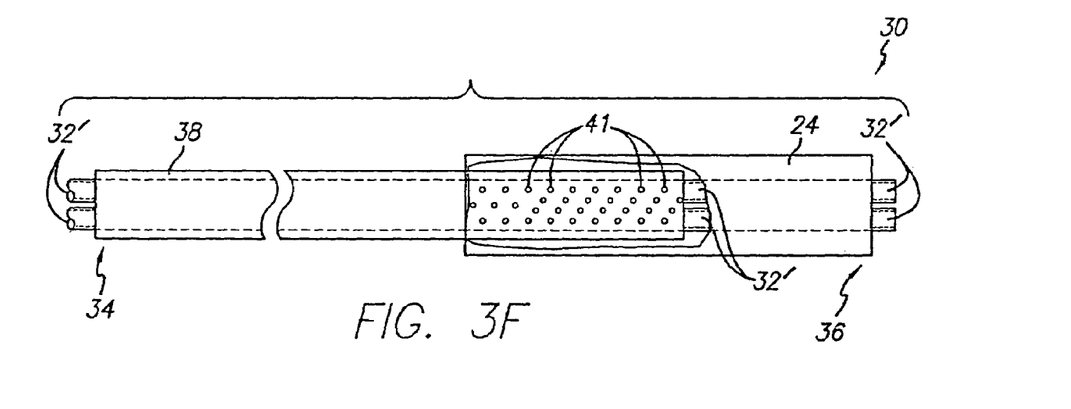
FIG. 3F is a sectional view of a variant of the seventh preferred embodiment of catheter shaft of FIG. 3C illustrating a pair of electrically conductive members.

In another presently preferred embodiment, illustrated in FIG. 3B, the apertures 40' can be axially oriented, helically arranged apertures formed as slits, channels or grooves. The apertures can be formed in the surface of the reinforcing tube by grinding or laser cutting, and allow the heating catheter to have a constant diameter, or a tapering diameter, from the proximal to the distal end of the shaft. In a presently preferred alternate embodiment illustrated in FIG. 3C, in which like elements are designated with like reference numerals, the apertures can be arranged in a pattern of a varying density, such as in a gradient, of round holes 41, which can be formed such as by laser cutting, helically arranged so as to provide a heating catheter that is torqueable and pushable at the proximal end, yet soft and flexible at the distal end. In another presently preferred aspect, the outer surface of the reinforcing tube can also be formed to have a taper (not shown) at the point where the helical apertures are formed in the reinforcing tube, such as by grinding or laser cutting, particularly at a distal portion of the reinforcing tube, to provide a heating catheter that is torqueable and pushable at the proximal end, yet soft and flexible at the distal end. As is illustrated in FIGS. 3D, 3E and 3F, the one or more electrically conductive members can be a pair of such electrically conductive wires 32', for example.

Figure 4A:
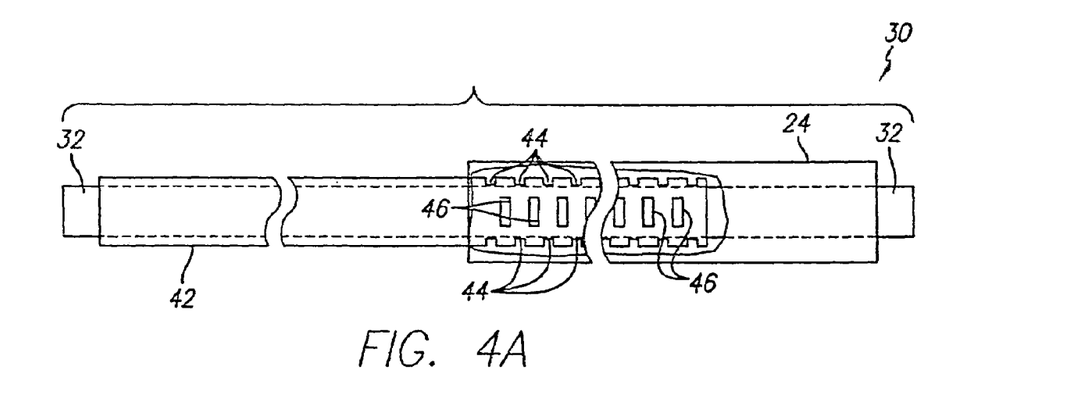
FIG. 4A is a schematic view of an eighth preferred embodiment of a variable stiffness optical shaft according to the invention.
Figure 4B:
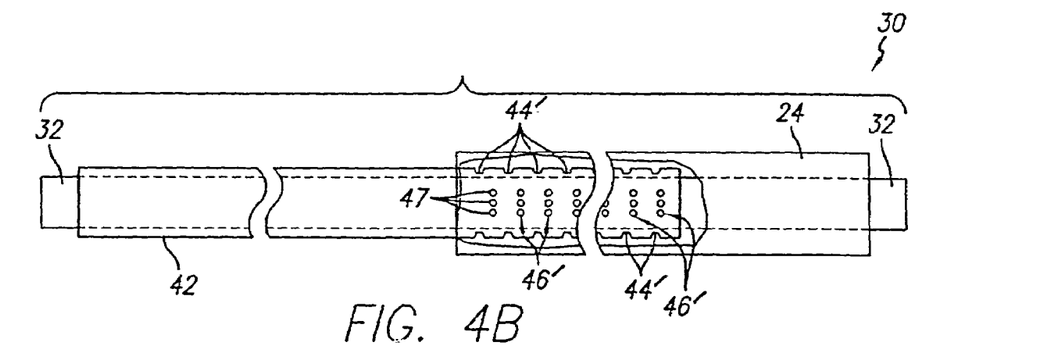
FIG. 4B is a schematic view of a ninth preferred embodiment of a variable stiffness optical shaft according to the invention.
Figure 4C:
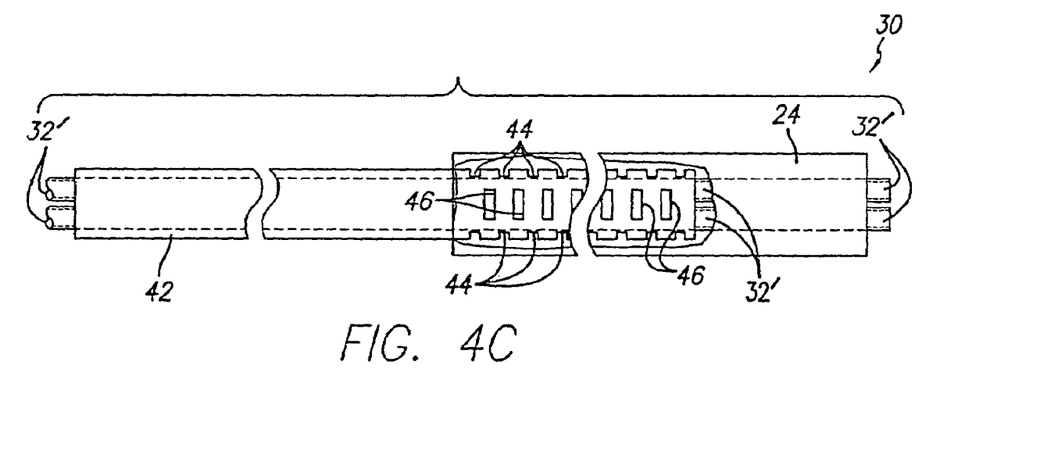
FIG. 4C is a sectional view of a variant of the eighth preferred embodiment of catheter shaft of FIG. 4A illustrating a pair of electrically conductive members.
Figure 4D:
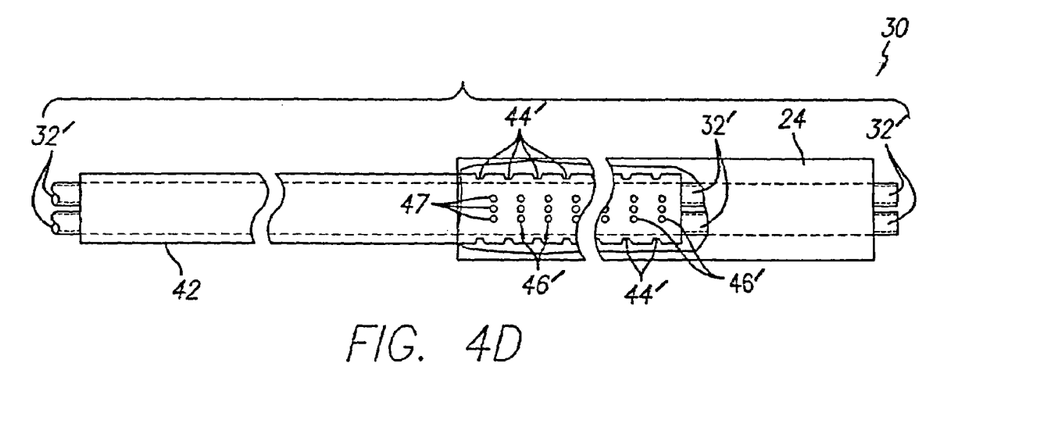
FIG. 4D is a sectional view of a variant of the ninth preferred embodiment of catheter shaft of FIG. 4B illustrating a pair of electrically conductive members.

In a further aspect of the invention illustrated in FIG. 4A, in which like elements are designated with like reference numerals, all or a portion of the shaft 42 can be formed with alternating laterally arranged apertures or cuts, slits, channels or grooves 44, 46 in the reinforcement tube to produce a composite shaft that has desired flexibility in a specific area of the shaft. Such a configuration can include variable width and depth of the apertures 44, 46 in order to vary the flexibility, torqueability and pushability of the shaft. In a presently preferred alternate embodiment illustrated in FIG. 4B, in which like elements are designated with like reference numerals, the laterally arranged apertures can be formed as groups 44', 46' of round apertures 47, formed such as by laser cutting, for example. As is illustrated in FIGS. 4C and 4D, the one or more electrically conductive members can be a pair of such electrically conductive wires 32', for example.

As described above, at least one coaxial outer covering or sheath 24 is also provided over at least a portion of the heating catheter and the reinforcing tube, for providing desired variations in stiffness along at least a portion of the length of the shaft. Such an outer sheath is currently preferably a heat shrink polymer, such as polyethylene, PTFE, PEEK, PET or PPS, for example, although other similar heat shrink polymers may also be suitable. Alternatively, the outer sheath can be a metal tube, such as a metal tube formed from a nickel titanium alloy, for example, that can be bonded adhesively over the outer surface of the heating catheter, such as by cyanoacrylate adhesive.

The one or more coaxial layers can be formed of heat shrink polymeric material, such as polyethylene, polytetrafluoroethylene (PTFE) polyethylene terephthalate (PET), polyetherethylketone (PEEK, also known as polyaryletherketone), polyphenylenesulfide (PPS), or any of a variety of other polymers which can be fabricated into a structure and necked or shrunk over a shaft, or can be formed of metal. While the invention can effectively use tubes which are placed over the exterior of the heating catheter shaft and then heat shrunk or bonded by adhesive to the heating catheter shaft, it is also contemplated that the shaft can be reinforced by other longitudinally extending additional structures with varying cross sections for certain specific applications.

The heat shrink tubing is placed on the heating catheter shaft, and then heat can be applied to the heat shrink tubing, resulting in shrinkage of the heat shrink tubing to encapsulate the heating catheter shaft. The structure formed by the apertures in the surface of the reinforcing tube, in combination with the distal taper of the reinforcing tube and outer coaxial sheath, allows the proximal part of the composite shaft to be relatively stiff, and the distal tip to be flexible and soft. A variety of other techniques can be used within the scope of the invention to accomplish the variable stiffness of the heating catheter shaft.

For neurovascular use, the overall length of a heating catheter pusher can be, for example, from 100 to 300 cm, with the outer diameter being less than about 1 French (0.0135 inch). For peripheral use, the overall length of the catheter can be, for example, from 100 to 300 cm, with the outer diameter of the distal 25 to 45 cm being less than about 5 French (0.063 inch), and the outer diameter of the proximal 100 cm being less than about 6 French (0.075 inch). For cardiovascular use, the overall length of the catheter can be, for example, from 150 to 175 cm, with the outer diameter of the distal 25 cm being less than about 3 French (0.038 inch), and the outer diameter of the proximal 100 cm being less than about 4 French (0.050 inch). These dimensions are approximate, and in practical terms, depend upon sizes of shrink tubing that are commercially available.

In practice, heating catheter shafts used for micro-coil delivery and the like are approximately 0.003 to approximately 0.014 inches in diameter, with the outer buffer comprising a layer of approximately 0.0005 to 0.002 inches in thickness of a polymer over a thin layer of cladding used to limit the dissipation of light out of the shaft. In one presently preferred embodiment, the outer buffer can be centerless ground to provide a variable thickness characteristic and the heating catheter shaft can be manufactured with a thicker than normal buffer to facilitate grinding of the buffer to provide a desired bending stiffness either with or without additional layers of stiffening polymers over the outer surface of the heating catheter shaft.

In one example of the method of manufacturing the variable stiffness heating catheter of the invention, the shaft can be assembled by sliding and centering a polyethylene coaxial heat shrink tube, which can be, for example, 200 cm in length, over a heating catheter, which can be, for example, 205 cm long. The ends of the heating catheter are then clamped, and tension is applied to keep the heating catheter taut. The proximal end of the polyethylene heat shrink tube is placed into the working area of a heat gun, although other means of controllably heating the heat shrink polymeric sheath may be used. The temperature of the polyethylene heat shrink tube is heated to approximately 650 F, and the rest of the heat shrink tube is heated by sliding the heat gun along the axis of the heat shrink tube at about three inches per second, for example, until the heat gun has traveled the length of the polymeric material and the polyethylene has encapsulated the heating catheter shaft. This method is repeated for 150 cm and 100 cm lengths of polymeric tubing, and any further heat shrink tubing to be used for varying the stiffness of the heating catheter, until the outside diameter of the shaft is built up to the desired dimensions to yield the desired degrees of stiffness.

Those skilled in the art will recognize that a variety of polymers, including those filled with reinforcing fibers or other material may be used to reinforce a heating catheter so that it can be more effectively used as a pusher within a catheter lumen or as a free therapeutic member. For example, the characteristics of the materials to be used may be optimized by use of abutting adjacent covers of different materials against one another longitudinally in end to end fashion to thus provide a constant outer diameter. In such a construction, the outer sheath is joined by heat and/or pressure or adhering bonded sections surrounding specific portions of the heating catheter, to provide a smooth overall exterior to the finished composite shaft.

It will be apparent from the foregoing that while particular forms of the invention have been illustrated and described, various modifications can be made without departing from the spirit and scope of the invention. For example, some of the various techniques of the invention can be advantageously combined for certain applications, while others are effectively met by only one aspect of the embodiments discussed. Accordingly, it is not intended that the invention be limited, except as by the appended claims.

What claimed is:

1. A variable stiffness catheter for use in interventional vascular therapy, comprising:
    a catheter shaft having a proximal portion and a distal portion, said catheter shaft including a pair of electrically conductive wires for providing resistive heating;
    a reinforcing tube having a proximal portion and a distal portion, the reinforcing tube surrounding the catheter shaft, and the distal portion of said reinforcing tube having a surface defining a plurality of apertures to provide variations in stiffness along the length of the catheter shaft; and
    at least one outer coaxial sheath over at least a portion of said catheter shaft and covering said plurality of apertures of said reinforcing tube.

2. The variable stiffness catheter of claim 1, wherein said plurality of apertures comprise axial slits formed in the surface of the reinforcing tube.

3. The variable stiffness catheter of claim 1, wherein the apertures can be formed as helical slits in the surface of the reinforcing tube.

4. The variable stiffness catheter of claim 1, wherein the outer surface of the reinforcing tube is tapered along its length.

5. The variable stiffness catheter of claim 1, wherein the apertures comprise a plurality of lateral slits formed in the surface of the reinforcing tube.

6. The variable stiffness catheter of claim 1, wherein said plurality of apertures in said reinforcing tube are disposed at the distal portion of said catheter shaft.

7. The variable stiffness catheter of claim 1, wherein the outer surface of the reinforcing tube is tapered at the distal portion of the reinforcing tube, whereby said catheter is torqueable and pushable at the proximal portion, yet soft and flexible at the distal portion.

8. The variable stiffness catheter of claim 1, wherein said outer coaxial sheath is formed from a material selected from the group consisting of a polymer, metal, or a combination thereof.

9. The variable stiffness catheter of claim 8, wherein said polymer comprises heat shrink polymeric material.

10. The variable stiffness catheter of claim 9, wherein said polymer is selected from the group consisting of polyethylene, polytetrafluoroethylene, polyethylene terephthalate, polyetherethylketone, and polyphenylenesulfide.

* * * * *